(12) United States Patent
Portney

(10) Patent No.: US 9,248,247 B2
(45) Date of Patent: Feb. 2, 2016

(54) CAPSULAR MEDICATION DELIVERY AND INHALATION DEVICE

(71) Applicant: Nathaniel Gerald Portney, San Diego, CA (US)

(72) Inventor: Nathaniel Gerald Portney, San Diego, CA (US)

( * ) Notice: Subject to any disclaimer, the term of this patent is extended or adjusted under 35 U.S.C. 154(b) by 365 days.

(21) Appl. No.: 13/951,345

(22) Filed: Jul. 25, 2013

(65) Prior Publication Data

US 2014/0026887 A1 Jan. 30, 2014

Related U.S. Application Data

(60) Provisional application No. 61/676,195, filed on Jul. 26, 2012.

(51) Int. Cl.
| | | |
|---|---|---|
| *A61M 15/00* | (2006.01) | |
| *A61M 11/00* | (2006.01) | |
| B65D 83/04 | (2006.01) | |
| A61J 1/03 | (2006.01) | |

(52) U.S. Cl.
CPC ........... *A61M 15/0028* (2013.01); *A61M 11/00* (2013.01); *A61M 15/0045* (2013.01); *A61J 1/035* (2013.01); *A61M 15/004* (2014.02); *A61M 15/009* (2013.01); *A61M 15/0035* (2014.02); *A61M 15/0038* (2014.02); *A61M 15/0048* (2014.02); *A61M 2202/064* (2013.01); *B65D 83/0454* (2013.01)

(58) Field of Classification Search
CPC .......... A61M 15/0028; A61M 15/003; A61M 15/0031; A61M 15/0033; A61M 15/0035; A61M 15/0036; A61M 15/0038; A61M 15/004; A61M 15/0041; A61M 15/0043; A61M 15/0045; A61M 15/0046; A61M 15/005; A61M 15/0048; A61M 15/006; A61M 11/00; A61J 1/035; B65D 83/0454
See application file for complete search history.

(56) References Cited

U.S. PATENT DOCUMENTS

| | | | |
|---|---|---|---|
| 5,551,597 A * | 9/1996 | Lambelet, Jr. | ..... B65D 83/0463 206/531 |
| 5,947,118 A | 9/1999 | Hochrainer et al. | |
| 6,065,472 A * | 5/2000 | Anderson | ......... A61M 15/0045 128/200.18 |
| 7,296,567 B2 | 11/2007 | Mahon et al. | |
| 7,878,193 B2 | 2/2011 | Kladders et al. | |
| 7,954,486 B2 | 6/2011 | Papania et al. | |
| 7,984,827 B2 | 7/2011 | Hygema | |
| 8,001,965 B2 | 8/2011 | Kladders et al. | |
| 8,006,695 B2 | 8/2011 | Lulla et al. | |
| 8,156,936 B2 | 4/2012 | Steiner et al. | |
| 8,196,578 B2 | 6/2012 | Wendland | |
| 8,397,946 B2 | 3/2013 | Portney | |

(Continued)

FOREIGN PATENT DOCUMENTS

| | | |
|---|---|---|
| LT | 5875 B | 9/2012 |
| MX | 2012003444 A | 4/2012 |

(Continued)

*Primary Examiner* — Lynne Anderson
*Assistant Examiner* — Bradley Philips
(74) *Attorney, Agent, or Firm* — Hackler Daghighian & Martino

(57) ABSTRACT

A method and capsular medication delivery and inhalation device is used with a medication capsule. The capsule is free-standing in a capsule chamber and not secured in a fixed position. The capsule is moved with a moveable back wall and other cooperative structure into an opener which releases the medication inside the capsule. The device may include an aerosol stream for facilitating medication delivery. The device works with capsules of varying sizes and shapes.

20 Claims, 5 Drawing Sheets

(56) References Cited

U.S. PATENT DOCUMENTS

| | | | |
|---|---|---|---|
| 2003/0178024 A1* | 9/2003 | Allan | A61M 15/0045 128/200.24 |
| 2005/0084700 A1* | 4/2005 | Ede | B29C 45/0053 428/544 |
| 2009/0013994 A1* | 1/2009 | Jones | A61M 16/0495 128/200.23 |
| 2010/0307491 A1* | 12/2010 | Lastow | A61M 15/0045 128/203.12 |
| 2011/0256932 A1 | 10/2011 | Kim et al. | |
| 2012/0035760 A1 | 2/2012 | Portney | |
| 2013/0025593 A1 | 1/2013 | Anandampillai et al. | |
| 2013/0152924 A1 | 6/2013 | Dunne | |
| 2013/0152927 A1 | 6/2013 | Baillet et al. | |

FOREIGN PATENT DOCUMENTS

| | | |
|---|---|---|
| WO | 2012047181 A1 | 4/2012 |
| WO | 2012120419 A2 | 9/2012 |
| WO | 2013004921 A1 | 1/2013 |

* cited by examiner

CAPSULAR MEDICATION DELIVERY AND INHALATION DEVICE

CROSS-REFERENCE TO RELATED APPLICATIONS

The present application claims priority from the U.S. Provisional Patent Application No. 61/676,195 filed Jul. 26, 2012. This patent application is to be incorporated by reference in its entirety by this specific reference thereto.

DESCRIPTION

1. Field of the Invention

The present invention relates generally to a method and device for incrementally dispensing pressurized contents and more specifically to a method of a medication delivery in a capsular form for inhalation and a device to execute the capsular form of medication delivery for inhaling.

2. Background of the Invention

An aerosol can be defined as a system of solid or liquid particles suspended in air or other gaseous environment. There are a number of clinical advantages of inhalation aerosols over systemic therapy (oral and injection) such as, for instance, its localization to the target organ, which allows for a lower dose of the medication. The advantage of small doses use for effective therapy, reduces systemic exposure to medication and minimizes side effects, it also allows a cost saving due to lower dosage regimens.

Inhalation devices can be classified into 3 categories:
(1) Propellant-Driven Metered-Dose Inhalers (pMDIs);
(2) Dry Powder Inhalers (DPIs); and
(3) Nebulizer inhalers.

The fundamental components of pMDIs are an actuator, a metering valve, and a pressurized container that holds the medication suspension or solution (liquid product) and propellant. A propellant can be a high-pressure gas or, more commonly, liquefied gas. The high pressure gas drives the liquid product through a narrow nozzle where it is atomized into a fine spray. Liquefied compressed gases is a more common option in pMDIs where it is in the gaseous phase at atmospheric pressure but forms a liquid when compressed in the container which also holds a medication to be delivered. Upon the release, the high vapor pressure propellant supplies the energy for liquid product dispersion in the aerosol form. The benefit of the second option is a constant vapor pressure in the container throughout the liquid product's life to ensure more consistent dosing. A major challenge with pMDI system is that it requires basically three components: (1) the drug suspension that is delivered; (2) the propellant that provides the vapor carrier of liquid aerosol-vapor suspension; and (3) the lubricant which helps keep the mechanism smooth. Also needed is a pressure nozzle through which the flashing to vaporize the suspension takes place when it gets vaporized into atmospheric/ambient pressure.

The medication in a DPI is in the form of a finely milled powder in large aggregates, either alone or in combination with some carrier substance, commonly lactose. A turbulent air stream created by air jet breaks up the particles and carries them into the airways of the patient.

Nebulizers offer opportunities for aqueous formulations of biomolecules. The most frequently used methods of nebulization are the air jet (pneumatic nebulizer) and ultrasonic devices. The air jet nebulizer produces a stream of high air velocity that causes liquid to spray as a mist. The operation of a pneumatic nebulizer requires a pressurized gas supply as the driving force for liquid atomization. Compressed gas is delivered through a jet, causing a region of negative pressure. The solution is entrained into the gas stream and is sheared into a liquid drops with a baffle placed in the entrance of the aerosol stream to produce even smaller particles.

All the devices have some issue with improper doses of the medication administration. Another issue is that patients may run out of medication because of difficulty to monitor its dispensing. For instance, dosage with liquefied compressed gases varies with the ambient temperature, as it is higher at higher ambient temperature and lower at lower ambient temperature. Effort to introduce a dosage control leads to the device cost increase.

There is a significant effort to improve the aerosol dispensing device with dosage metering. For instance, U.S. Pat. No. 7,296,567 includes a breath actuation inhaler with an aerosol valve with a transient metering chamber. Another example of mechanical control is U.S. Pat. No. 7,984,827 where the rotation is precisely controlled. There is an effort to include disposable element that aerosolizes an active substance for delivery to a patient to prevent the substance from contacting non-disposable elements in order to minimize a contamination. See U.S. Pat. No. 7,954,486.

Another risk factor in current aerosol devices is a risk of contamination due to possibility of the contact between the active agent and the device part that are difficult or impossible to clean between the usages.

The delivery of the medication in the capsule form inherently resolves the issue of a contamination as well as dosage control and, therefore, presents a significant interest. Below are the descriptions of prior art involving capsule based inhalers. Hochrainer discloses in the U.S. Pat. No. 5,947,118 a capsule holder to be used in conjunction with inhaler. The capsule is fixed in the stationary position. Villax discloses in the U.S. Application Publication No. 2011/0269328 a capsule based inhaler for dry powder inhaling. The individual capsule is loaded in capsule chamber and aligned with air passage. Then a cutting means engages the top and bottom part of the capsule to open it out and the gas flow transports the dry powder from the capsule to the patient. Kladders discloses in the U.S. Pat. Nos. 7,878,193 and 8,001,965 the capsule based inhaler also shown by Hochrainer. Kladders discloses capsule design for the similar inhaler arrangement as described by Villax where a cylinder shaped capsule is loaded into the capsule chamber to align it certain way. The capsule is then opened usually in two longitudinal ends for the air flow to carry the capsule content to the patient. Lailla discloses in the U.S. Pat. No. 8,006,695 a variation of the inhaler design as described above that uses the same principle of loading the capsule in the capsule holder and then piercing the capsule to enable for the air flow through the capsule holder to carry the powder medication to the patient. Steiner discloses in the U.S. Pat. No. 8,156,936 the capsule based inhaler for dry powder delivery. The capsule is placed in a mixing chamber and is already open and the chamber can be open for the air flow to mix it with the dry powder of the capsule for the transportation to the patient. Wendland disclosed in the U.S. Pat. No. 8,196,578 the capsule based inhaler equivalent to Hochrainer and Kladders. Anandampillai discloses in the U.S. Patent Application Publication No. 2013/0025593 a dry power inhaler which does not uses a capsule but a blister strip with the dry powder. The strip is pierced and the powder is positive onto the drug material for mixing and the air flow transport the powder with drag to the patient. The system is likely limited in dosage control as involved a number of steps. Dunne discloses in the U.S. Patent Application Publication No. 2013/152924 a capsule based inhaler where capsule include a sealed prefabricated hole that is opened in the usage state. The inhaler principle of capsule operation is the same disclosed above in the prior art. Schulz discloses in the Application MX2012003444 the capsular based inhaler similar to one disclosed by Hochrainer, Kladders and Wendland. Baillet discloses in U.S. Patent Application Publication No. 2013/152927 a method of using a dry powder inhaler where also the capsule is loaded in specific orientation, opening the capsule to empty the dry powder into the dispersion chamber for inhaling by the patient. Baillet also discloses in the WO2013004921 an inhaler for dry powder of a different design but the same principle as above, i.e. the capsule is loaded in specific position, then opened and air flow disperses the powder. Pineschi discloses in the WO2012120419 a portable inhaler where a powder substance is held in a capsule-like container. Jose discloses in the LT5875 an inhalator with the capsule loading performing by the same principle as above. Bilgig discloses in the WO2012047181 an inhaler comprising capsule with dry powder form. Also, it is based on the same principle of capsule chamber for loading the capsule in specific orientation.

Thus, there is a need to provide a method and device capable to control dosage more accurately as allowed by the capsular format but, at the same time, without a need for specific capsule handling for alignment with precise opening by cutting means. There is also a need for multiple capsule arrangements without a need for a complex mechanism to load and align a capsule and precise piercing means movement. There is also a need to expand the capsule use to a fluid form for inhaling from the currently used dry powder form in the capsule based inhalers. The present invention fulfills these needs and provides other related advantages.

SUMMARY OF THE INVENTION

One novel aspect of the inhaling device of the present invention is the medication dose placement in the capsule form. It is an objective of the present invention to provide a method of medication dispensing by a capsule form for inhalation delivery and also to describe a capsular inhaling device (CED) to execute the method. The method and device can be used for ingesting delivery of a medication but the term inhalation is used through out this disclosure to cover both ingestion and inhalation.

The capsule of the disclosed method and device is in a free standing form meaning that the capsule with the medication for inhaling is not held in the loading chamber by a mechanical means for a particular position and/or alignment but the capsule is only supported by the walls of the loading chamber thus allowing the capsule to shift and move with the change in orientation of the loading chamber.

The method according to the present invention offers a preset dosage inherently and independently of the user ability to operate the device thus replacing a pressurized container with the medication as in pMDIs which is the primary cause of the dispensing variability. The method is based on the use of free-standing capsule in a loading chamber without a need for its alignment for opening by a piercing or cutting means. The capsule is transported from the loading chamber to a different location outside the loading chamber for capsule opening by a transporting mechanism of the inhaler. The separation of the function of loading and opening at different locations of the capsule is one key aspects of the method of the present invention which allows extending the inhaling device from a single capsule loading to a multiple capsules loading in a form of a cassette or cartridge consisting of multiple loading chambers.

Still another objective of the invention is to allow patient to use different medications in a form of inhalation by utilizing a single device. Capsules with different medications or their mix can be loaded into a single cartridge but different loading chambers for the use and the patient can choose which capsule to transport from the loading chamber for opening and consecutive inhalation by selecting the corresponding loading chamber. Multi-part capsule can be used with one part being a propellant to carry the medication upon capsule opening.

Another aspect of the present invention is to be able to open a capsule during its extraction or transportation from the loading chamber to a location outside the loading chamber instead of moving a piercing (opening) means as described in the prior art. This allows simplifying the overall mechanics because of the dual actions of capsule transportation and opening.

According to the present invention, the capsule opening is done with at one side, opposite sides or across the capsule depending on the capsule content by arranging the piercing or cutting means accordingly. The terms "piercing" is used through out the present invention disclosure as a general term of capsule opening.

A further aspect of the present invention is to be able to squeeze the capsule in its opened state for a full release of its content for an accurate dosage control. Squeezing can be performed between the dovetail type surfaces to be able to expose the capsule interior for its content full removal.

Still further aspect of the present invention is to include the content in a fluid form thus not limiting it only to a dry powder form of the prior art. The medication can be suspended in a fluid or as a solution similar to pMDIs and Nebulizers. It also can be in a dry form similar to DPIs. In case of a dry form, one of the options also is for a medication capsule to include two elements, one containing a dry form medication and another containing a fluid or propellant. Both elements pierced simultaneously for capsular inhaling operation for the fluid or propellant of the capsule to carry the dry form medication into the jet stream for inhaling.

Thus, the capsular construction of the inhaling device per the present invention allows replacing all three types of the inhaling devices used currently with one of a simple and compact form.

The U.S. Pat. No. 8,397,946 by Portney illustrates a mechanical dispenser which may be used as the mechanical manipulating part of the present invention, however other dispenser systems may be utilized. The U.S. Pat. No. 8,397,946 is to be incorporated herein in its entirety by this specific reference hereto with the specified modification for capsule based inhalation. One central part of the present invention is the modification of the cartridge and interaction of the cartridge with the dispenser housing to enable manipulation of the capsule for the purpose of transposing it from the cartridge sector acting as the loading chamber to a different location for capsule opening, squeezed (optional) and to turn on a jet stream to transport the capsule content to the patient for inhalation.

U.S. patent application Ser. No. 13/204,407 (Publication No. 2012/0035760) by Portney is to be incorporated herein in its entirety for electronic control of the capsule dispensing with this reference.

The capsule form of medication delivery loaded in a cartridge offers also a benefit of capsule loading of the cartridge placed within the dispenser, i.e. without removing the cartridge. The loading can be electronically registered with the cartridge movement to a different loading chamber for capsule (pill) loading. The method of loading can be used for the inhaling device of the present invention as well for a general loading with the pill of the device described in the U.S. Pat. No. 8,397,946.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

The dispenser's overall mechanical construction is described in the U.S. Pat. No. 8,397,946. There are several modifications to execute the method of providing medication in the capsular form where the medication is released for inhaling.

Figure 1A:
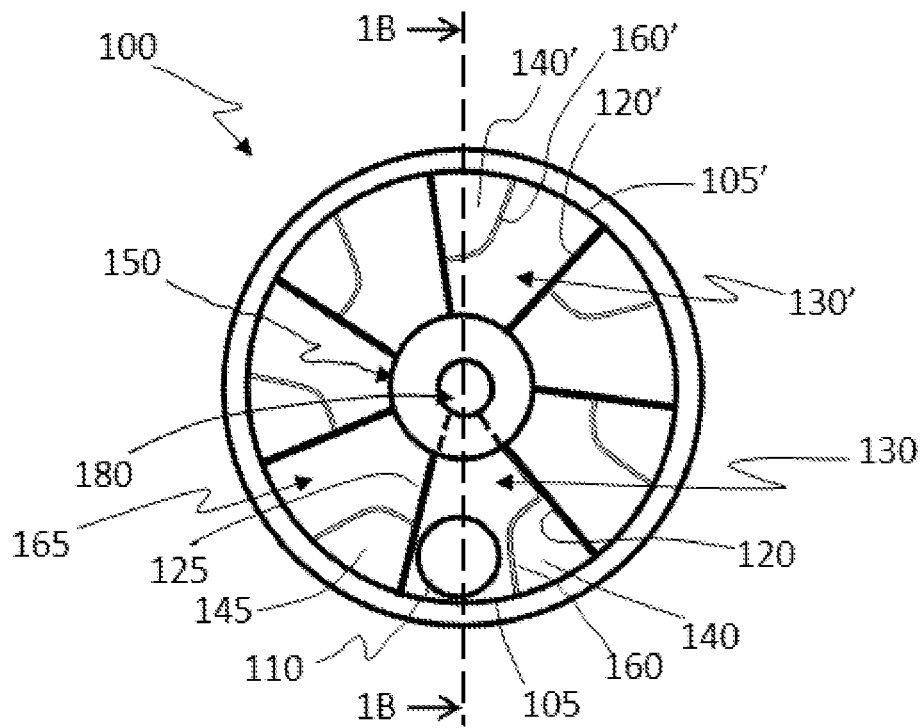
FIG. 1A demonstrates an exemplary embodiment of the present invention showing a cartridge front view without a front cover.

In summary, FIG. 1A demonstrates the cartridge front view without a front cover. A single capsule is shown in the cartridge sector acting as a loading chamber for illustration as any of the sectors can be loaded with a capsule. The sectors are shown of equivalent size and shapes but, generally, they can be of different sizes and shapes to accommodate capsules.

Figure 1B:
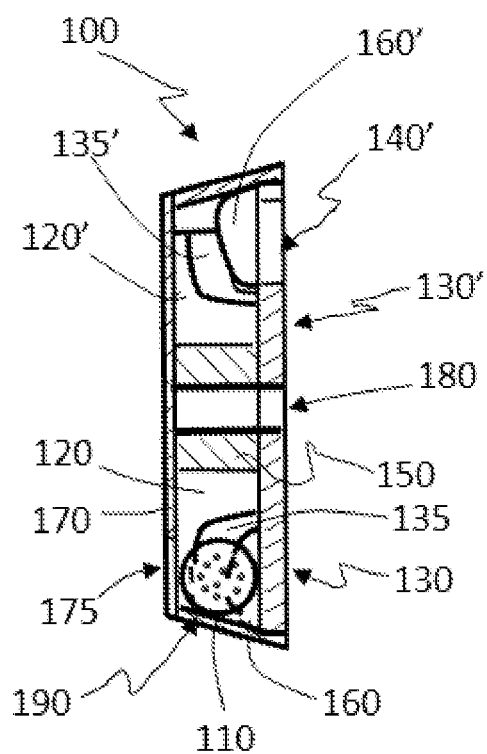
FIG. 1B is a sectional view of the structure of FIG. 1A taken along line 1B-1B.

FIG. 1B demonstrates a cross-section of the cartridge of the FIG. 1A for additional explanation. The same loading setup with a single capsule is used in the following figures. Cartridge overall shape and size as per the U.S. Pat. No. 8,397,946 is used in the figures describing the present invention for illustration purpose only as a single capsule loading or capsule cassette loading or different cartridge shape loading are also optional per the present invention. The reference to the term "cartridge" is used through out the disclosure of the present invention with the understanding that this term encompasses all described above different options of the capsule loading chamber.

Figure 2A:
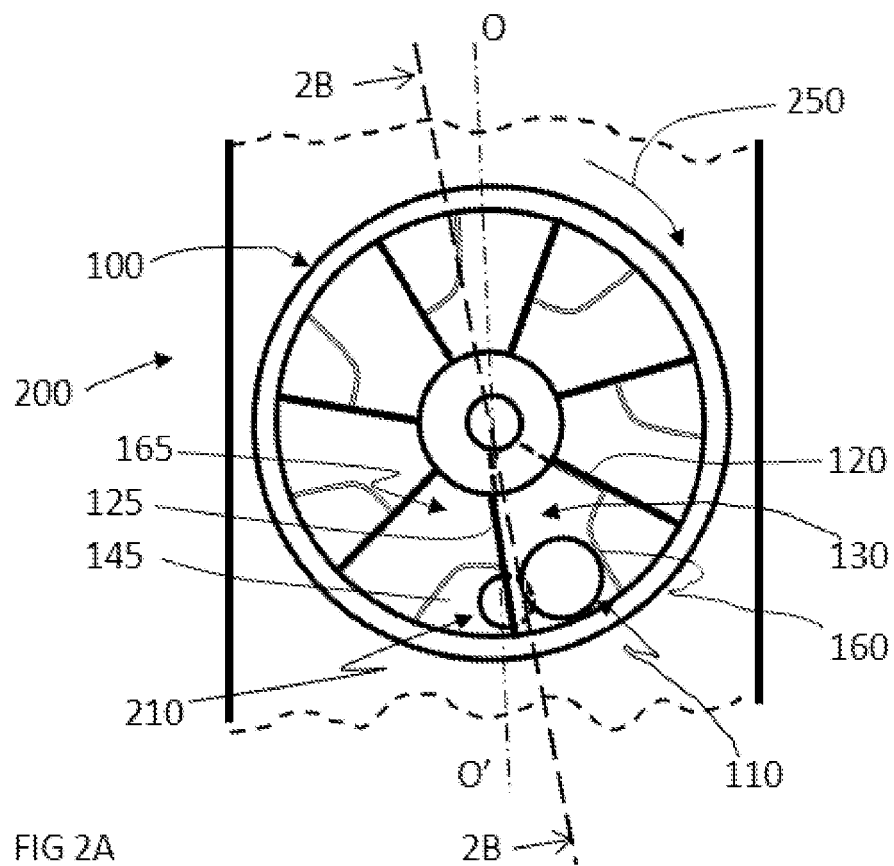
FIG. 2A is similar to FIG. 1A now showing rotation of the cartridge and engagement with a pusher.

FIG. 2A illustrates front view of the cartridge in dispenser where the figure encompasses only a portion of the dispenser with the cartridge. The cartridge is shown with a single capsule located at the sector in the sector position A. The sector at or close to the position A is the "initial" position as the capsule is largely located within the sector just before being transported out of the cartridge sector for capsule opening.

Figure 2B:
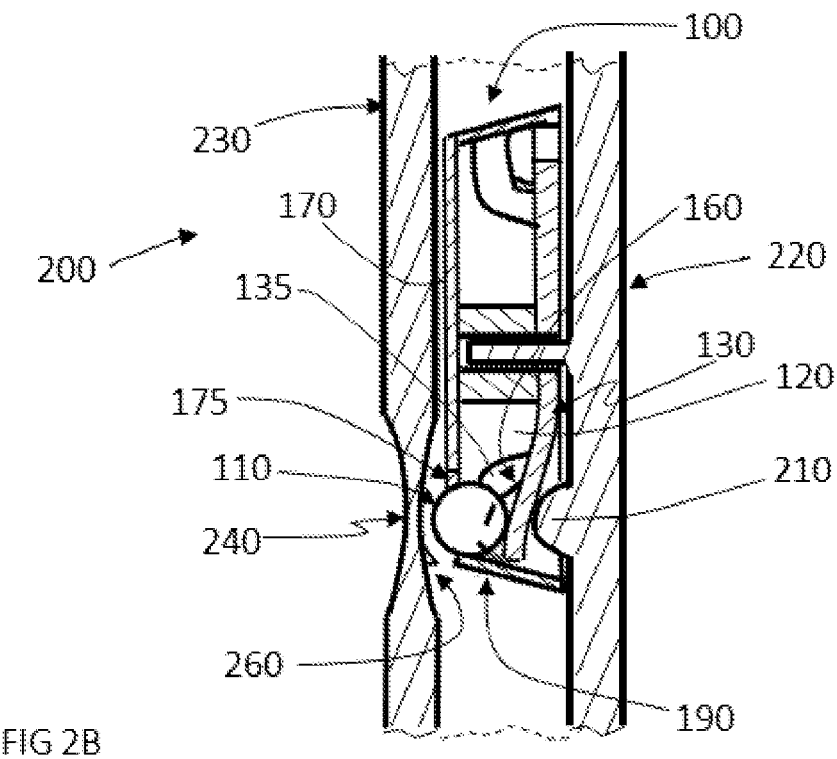
FIG. 2B is a sectional view of the structure of FIG. 2A taken along line 2B-2B.

FIG. 2B demonstrates a cross-section of the cartridge of the FIG. 2A for additional explanation particularly modifications in the dispenser construction from the one described in the U.S. Pat. No. 8,397,946.

Figure 3A:
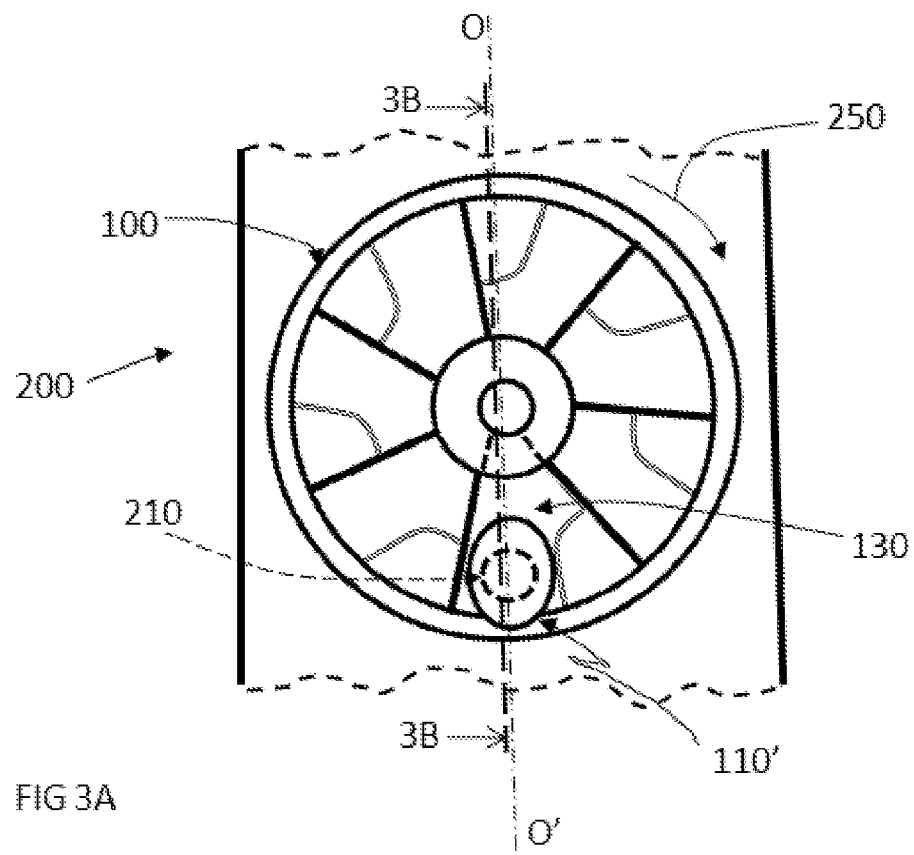
FIG. 3A is similar to FIG. 1A and 2A now showing further rotation of the cartridge.

FIG. 3A illustrates front view of the cartridge in dispenser where the figure encompasses only a portion of the dispenser with the cartridge. The cartridge is shown in the sector in the sector position B where the capsule fully transported out of the sector of the cartridge. The capsule is also shown to be squeezed which is only an option. Another option is to transport the capsule to a chamber outside the loading chamber for capsule consecutive manipulation (alignment, heating, applying electrical charge, dissolving, etc.).

Figure 3B:
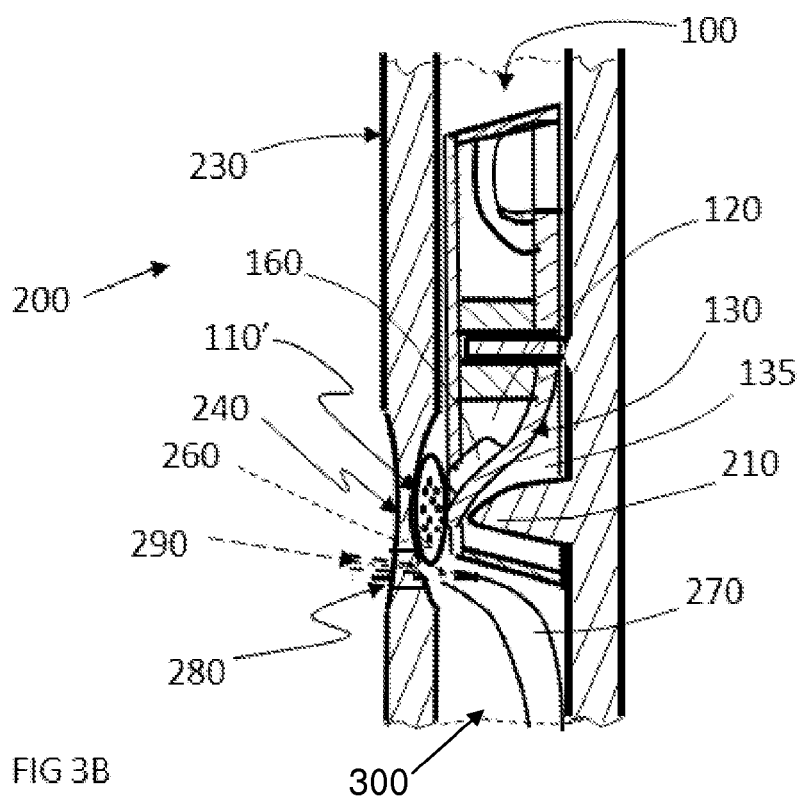
FIG. 3B is a sectional view of the structure of FIG. 3A taken along line 3B-3B.

FIG. 3B demonstrates a cross-section of the dispenser with the cartridge of the FIG. 3A for additional explanation.

Figure 4A:
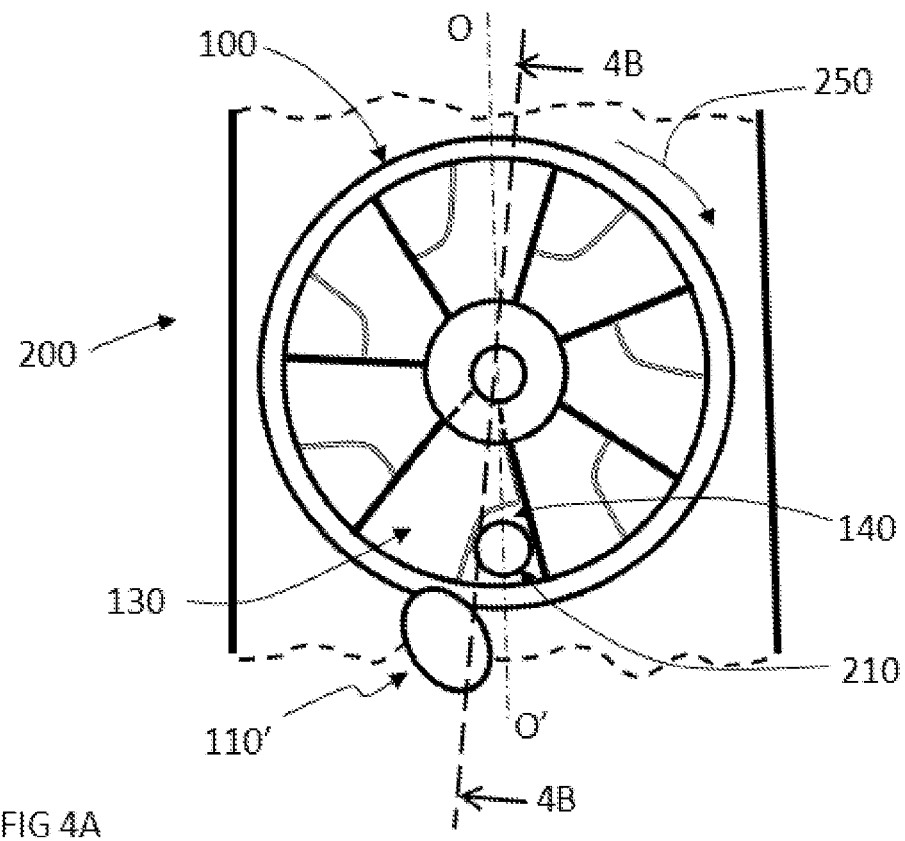
FIG. 4A is similar to FIG. 1A, 2A and 3A now showing further rotation of the cartridge.

FIG. 4A illustrates front view of the cartridge in dispenser where the figure encompasses only a portion of the dispenser with the cartridge. The cartridge is shown in the sector position C where the content of the capsule has been extracted and the remaining capsule shell is released for a disposal.

FIG. 2B demonstrates a cross-section of the dispenser with the cartridge of the FIG. 4A for additional explanation.

Figure 5:
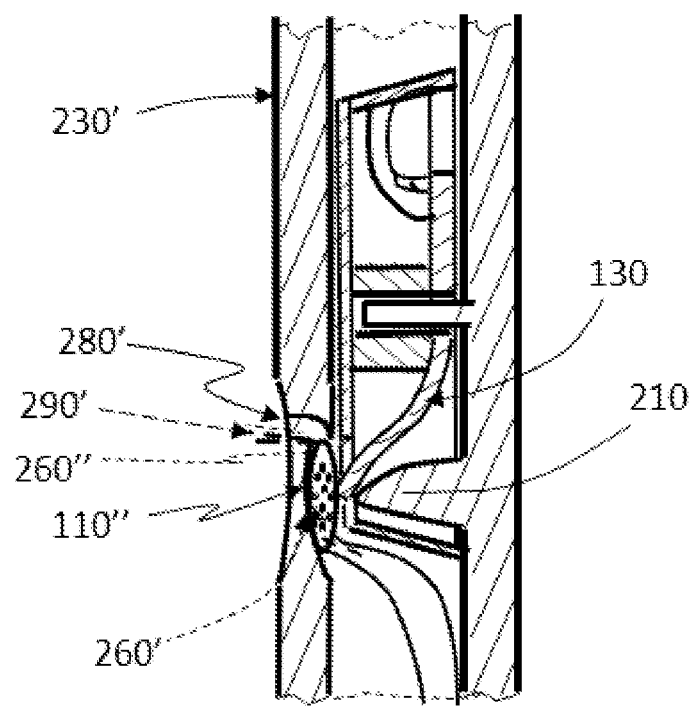
FIG. 5 is similar to FIG. 3B now showing the jet-stream flowing through the capsule.

FIG. 5 demonstrates a cross-section of the cartridge with dispenser in the sector position B where the jet-stream flows through the capsule to carry its content which is particularly useful dry powder application for inhaling.

Now in more detail, FIG. 1A illustrates a cartridge 100 which is largely of a circular shape and divided into sectors/capsule chambers 105, 105' and so on for loading individual capsules in each capsule chamber. The cartridge 100 is shown with seven capsule chambers but their numbers and dimensions may vary. A capsule 110 is loaded in the capsule chamber 105. The rounded shape of the capsule 110 is used for illustration purposes as a preferable shape but a cylindrical shape or other shapes are also an option.

The descriptions are referenced to one or two selected capsule chambers but the same is applicable to all other capsule chambers. Each capsule chambers 105 and 105' are bordered by sector leaves/moveable back walls 130 and 130' correspondingly at the back or rear of the capsule chambers 105. The moveable back walls 130 are separated by divider walls such as 120, 120' and so on. All moveable back walls are fixed at their central portion at the cartridge center by the sector leaf holder/moveable wall holder 150 so that the rest portion of a moveable back wall can freely bend forward within the sectors between the divider walls 120. This is similar to a cantilevered structure. The moveable back wall 130 is attached near the common axis of rotation and the other end is cantilevered, free to move when biased by other structures and forces.

There is a cartridge hole 180 within the moveable wall holder 150 for cartridge 100 placement into a cartridge dispenser or housing 200.

Each moveable back wall or sector leaf includes an opening 140 and 145. For instance, moveable back walls/sector leaves 130 and 130' include the openings 140 and 140' correspondingly. There is also an opening 145 in the moveable back wall 165 neighboring the moveable back wall 130. Each opening has a divider wall 120 and 125 on one side and opening wall 160 and 160' on the other side. The opening wall 160 is a wall that borders the opening 145. For instance, the opening 140 has sector divider 120 on one side and opening wall 160 on the other side. The opening wall 160' is also shown for the opening 140'. The cartridge hole 180 is formed and opening wall 160' is attached to the corresponding sector leaves 130 and 130'. The capsule 110 is located between the divider wall 125 and opening wall 160 in the cartridge 100 placed vertically with the capsule chamber 105 being in the lowest position.

FIG. 1B manifests the cross-section 1B-1B of the FIG. 1A to demonstrate the cartridge construction in more details. It shows the opening wall 160 to be relatively low but still adequate to maintain the capsule 110 at the periphery of the moveable back wall 130 in the cartridge vertical orientation. The capsule 110 is supported by the periphery/outer radius wall 190 of the cartridge 100 and within the cover/cartridge front wall 170, opening wall 160, and divider 125 shown on FIG. 1A. The opening wall 160 may be attached to the moveable back wall 130 or alternatively attached to the outer radius wall 190. Thus, the capsule movement is restricted when the capsule 110 is located in the lowest sector with cartridge 100 being placed vertically as dictated by the gravity. The cover 170 includes a capsule extraction hole 175 located at the capsule 110 position at the sector periphery. Similar holes are placed at the periphery of all capsule chambers. A capsule extraction hole is sized slightly smaller the size of the capsule placed in the corresponding sector to keep the capsule within the sector but large enough for the capsule to be pushed through the hole by a reasonable force. A capsule 110 can be made of flexible shell to allow a deformation and/or a hole includes diagonal a cut-outs allowing its rim for its expansion to a larger size in case if a capsule is made of a hard shall and pushed through the hole.

The divider walls 120 may include a divider wall opening 135 shaped to keep a capsule within the corresponding capsule chamber for the sector leaf pusher 210 (explained below) to pass from one sector to next sector. The opening wall 160 is high enough to keep the capsule 160 at a certain location within the capsule chamber and low enough to avoid interference with the front cover of the cartridge when the moveable back wall/sector leaf is bent.

The upper capsule chamber construction is also shown in the FIG. 1B and one can see the divider wall 120', sector divider opening 135', moveable back wall or sector leaf 130' with opening 140' and opening wall 160'.

The sector leaves/moveable back walls are held in position at the back of the cartridge by sector leaf holder/moveable wall holder 150 with the cartridge hole 180 for the cartridge attachment to a dispenser.

The following figures illustrate the method of transferring a capsule for the loading chamber, then opening it for inhaling and then dispensing the capsule shell.

FIG. 2A illustrates front view of the cartridge 100 inside the dispenser/housing 200 in so called initial position A where the capsule 110 is largely within the sector (loading chamber) of the dispenser and the sector is in its lowest position when the dispenser with the cartridge placed vertically.

The portion of the dispenser 200 is shown that includes the cartridge 100 and along the vertical orientation of the axis O-O'. The capsule 110 is supported at the back side by the sector leaf/moveable back wall 130 placed between the wall dividers 120 and 125 to guide the leaf movement within these dividers. Equivalent structure is applied to all sectors of the cartridge. The capsule 110 is pushed by the wall opening 160 as the cartridge is rotated clock-wise as shown by the arrow 250. The sector leaf/moveable back wall 130 comes into contact with the sector leaf pusher/incline feature/protrusion 210 largely located within the sector opening 145 of the neighboring capsule chamber 165. The sector leaf pusher/incline feature/protrusion 210 is lined up with the axis O-O'.

In the initial position A the sector leaf pusher 210 is largely within the sector opening 145 to allow the moveable back wall 130 to be in flat position.

FIG. 2B demonstrates 2B-2B cross-section of the FIG. 2A to explain the additional details of the sector position A. The sector leaf/moveable back wall 130 is only slightly bent by the sector leaf pusher 210 represented as a bump of the appropriate size at the back wall 220 of the dispenser/housing 200. The capsule 110 is shown only partially protruded though the capsule extraction hole 175 placed at the front cover 170 of the cartridge 100 and close to the cartridge periphery 190 where the capsule 110 is located. The capsule 110 is pushed by the opening wall 160 attached to the sector leaf/moveable back wall 130. The sector leaf pusher 210 is passing through the sector divider opening sized similar to the divider opening 135 of the sector divider 120.

FIG. 2B also demonstrates two features of the front wall 230 of the dispenser. There is dispenser front wall thinning 240 at the location of the capsule protruded through the capsule extraction hole in the sector position A. This is to allow some flexibility of the front wall when interacting with a capsule. There is also piercing means 260 facing the capsule at the back of the dispenser front wall 230. A single position of the piercing means 260 is shown at the level of the bottom part of the capsule 110 in order to pierce a capsule at its bottom part. A piercing means can also be placed at the level of the top part of the capsule to pierce a capsule at its top part or at both places.

FIG. 3A demonstrates the next phase of the cartridge 100 clock-wise rotation repressed by the arrow 250 where the capsule 110' now is closely aligned with the sector leaf pusher 210 leading the capsule 110' to be pushed out of the sector and pressed against the front wall 230 of the dispenser 200 by the sector leaf/moveable back wall 130. The capsule 110' together with the sector leaf pusher 210 are lined up with the axis O-O'. The capsule 110' is shown flatten which occurs if it is made of a soft shall and it releases its content upon the shell piercing and capsule squeezing. This is the position of a maximum bending of the sector leaf/moveable back wall 130 to fully extract the capsule from the cartridge and compress it against the front wall 230 of the dispenser/housing 200.

FIG. 3B demonstrates a cross-section 3B-3B of the FIG. 3A closely aligned with the axis O-O'. The cartridge 100 is turned now to the position B where the capsule 110' is transported out of the corresponding sector acting as the loading chamber and flattened by the sector leaf/moveable back wall 130 against the thinning portion 240 of the front wall 230 of the dispenser 200. A slight flexing of the dispenser front wall thinning 240 helps in providing enough space between the front wall 230 of the dispenser 200 and cartridge 100 for a full extraction of the capsule 110' from the cartridge 100.

The combination of the sector leaf/moveable back wall 130 fixed at one side and bent by the sector leaf pusher 210 act as the transporting mechanism for extracting the capsule from the sector function as the loading chamber for capsule opening outside the sector by the piercing or cutting means 260. The divider wall opening 135 attached to the moveable back wall/sector leaf 130 is shown low enough to avoid interference with the front cover 170 of the cartridge. The divider wall opening 135 is also visible behind the moveable back wall/sector leaf 130. The described transporting mechanism for capsule extracting from the loading chamber to a location outside the loading chamber is not limited by this particular arrangement and a different mechanism construction is possible.

The piercer or piercing means 260 opens the capsule 110' at its lower portion for the medication release. The piercer 260 can be a mechanical needle or small blade or even of an electrical nature as an electric spark or a laser beam.

The cartridge rotation is a fairly fast process as well as the medication release from the capsule so the released medication gains some kinetic energy. The dispenser 200 includes the replaceable canister with the pressurized gas or liquefied compressed gas similar to one used in a pMDI to provide more consistent pressure. The gas release is synchronized with the position B when the medication is released from the capsule to supply high kinetic energy to medication which is a liquid mix or dry powder to be dispersed in the aerosol stream 290, 270 through the aerosol stream hole 280. It could be also a mouthpiece attached at the front wall of the dispenser 200 where the aerosol stream hole 280 is to direct the aerosol stream 290 to the patient's mouth for inhaling. A mouthpiece can be a disposable element to further minimize a contamination.

FIG. 4A explains the final sector position C of the cartridge 100 upon the capsule 110' disposal. Cartridge 100 rotation shown by arrow 250 beyond the axis O-O' brings the sector leaf pusher 210 into the sector opening 140 thus letting the sector leaf/moveable back wall 130 to take a flat form and to release the capsule 110' for it to drop into a disposing bin at the bottom of the dispenser 200.

Figure 4B:
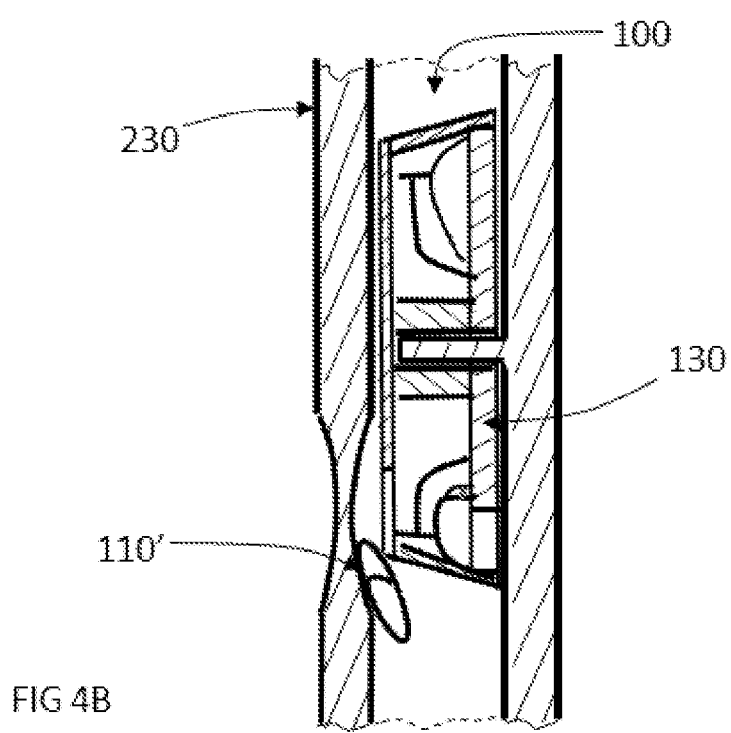
FIG. 4B is a sectional view of the structure of FIG. 4A taken along line 4B-4B.

FIG. 4B demonstrates a cross-section 4B-4B of FIG. 4A in the sector position C. The sector leaf/moveable back wall 130 is in a flat and unbent state and the flattened capsule 110' is shown to fall down by gravity within the space between the cartridge 100 and dispenser front wall 230 into a dispenser disposing bin.

The consecutive sector is in the position A now as the initial phase of the cartridge rotation to process next capsule and process is repeated again.

FIG. 5 is similar to FIG. 3B above to demonstrate a cartridge in the sector position B where the aerosol stream 290' passes through the capsule 110" which is particularly useful in case of a dry powder content. The capsule 110" is shown flattened by the sector leaf/moveable back wall 130 bent by the sector leaf pusher 210 as an option as the main function of the sector leaf pusher is to transport a capsule out of the capsule chamber of a cartridge. A capsule might include a hard shell to maintain its shape without being flatten which might be useful for a dry powder content.

The piercers 260' and 260" are located at the dispenser wall 230' in order to interact with the bottom and top parts of the capsule 110" and allow the aerosol stream 290' to pass through the capsule and then through the aerosol stream hole 280' placed close at the top of the capsule. It is also possible to include a piercer at the edge of the capsule extracting hole of a cartridge. A sharp edge serving as a piercer may be at the bottom of the hole to open the bottom part of the capsule when it is pushed though the hole out of the loading chamber or at the opposite sides of the hole to open the capsule at the bottom and top parts of the capsule when it is pushed though the capsule extracting hole. Similar to the explanation of FIG. 3B, the gas release is synchronized with the position B when the medication is released from the capsule to supply a high kinetic energy to medication which is a liquid mix or dry powder to disperse in the aerosol stream.

A canister with the pressurized gas or liquefied compressed gas (pressurized pneumatic container) may be used for medication dispersion in the aerosol stream 270 for inhalation. The canister would be connected to a port 300. The canister can be synchronized with rotation of the 100 such that when the capsule 110 is opened, the canister releases the pressurized gas.

Although several embodiments have been described in detail for purposes of illustration, various modifications may be made to each without departing from the scope and spirit of the invention. Accordingly, the invention is not to be limited, except as by the appended claims.

What is claimed is:

1. A medication delivery device, comprising:
   a housing;
   a plurality of capsule chambers radially disposed about a common axis of rotation, the plurality of capsule chambers rotatably connected to the housing;
   a moveable back wall disposed in each of the plurality of capsule chambers, each moveable back wall configured to move in a direction along the common axis of rotation configured to move a capsule located within each capsule chamber to a position outside each capsule chamber or adjacent to each capsule chamber;
   a capsule opener attached to the housing; and
   an incline feature connected to the housing disposed inline with the capsule opener behind the moveable back walls, the incline feature configured to bias at least one of the moveable back walls towards the capsule opener when the plurality of capsule chambers rotates about the common axis of rotation.

2. The device of claim 1, wherein each capsule chamber of the plurality of capsule chambers comprises a first divider wall abutting an outer radius wall, the outer radius wall abutting a second divider wall.

3. The device of claim 1, including an opening formed in a portion of the moveable back wall at a common radius to the incline feature, the opening configured accept the incline feature without moving the moveable back wall.

4. The device of claim 3, including an opening wall adjacent to the opening configured to prevent the capsule from passing through the opening.

5. The device of claim 1, wherein the moveable back wall is cantilevered and attached near an inner radius adjacent to the common axis of rotation.

6. The device of claim 1, including a port connected to the housing configured to be attachable to a pressurized pneumatic container.

7. The device of claim 6, including a passageway formed form the port to an aerosol stream hole adjacent to or near the capsule opener.

8. The device of claim 1, wherein the capsule opener comprises a piercer, a needle, a blade, an electric spark or a laser beam.

9. The device of claim 1, wherein the housing comprises a front wall opposite a back wall, wherein the plurality of capsule chambers are disposed between the front wall and back wall.

10. The device of claim 9, wherein the capsule opener is attached to the front wall and wherein the incline feature is attached to the back wall.

11. The device of claim 10, wherein the front wall comprises a thinning disposed adjacent to the capsule opener and aligned with the incline feature.

12. The device of claim 1, including an aerosol stream hole disposed within the front wall adjacent to the capsule opener.

13. A medication delivery device, comprising:
   a housing comprising a front wall opposite a back wall;
   a plurality of capsule chambers radially disposed about a common axis of rotation, the plurality of capsule chambers rotatably connected to the housing between the front wall and back wall of the housing;

a moveable back wall disposed in each of the plurality of capsule chambers, each moveable back wall configured to move in a direction along the common axis of rotation configured to move a capsule located within each capsule chamber to a position outside each capsule chamber or adjacent to each capsule chamber;

a capsule opener disposed in front of the moveable back wall, the capsule opener attached to the front wall of the housing or attached to the plurality of capsule chambers; and an incline feature connected to the back wall of the housing disposed inline with the capsule opener behind the moveable back walls, the incline feature configured to bias at least one of the moveable back walls towards the capsule opener when the plurality of capsule chambers rotates about the common axis of rotation.

14. The device of claim 13, including an opening formed in a portion of the moveable back wall at a common radius to the incline feature, the opening configured accept the incline feature without moving the moveable back wall.

15. The device of claim 14, including an opening wall adjacent to the opening configured to prevent the capsule from passing through the opening.

16. The device of claim 15, wherein the moveable back wall is cantilevered and attached near an inner radius adjacent to the common axis of rotation.

17. The device of claim 16, wherein the front wall of the housing comprises a thinning disposed adjacent to the capsule opener and aligned with the incline feature.

18. A medication delivery device, comprising:
a housing;
at least one capsule chamber radially disposed about a common axis of rotation and rotatably connected to the housing;
a moveable back wall disposed in the at least one capsule chamber, the moveable back wall configured to move a capsule located within the at least one capsule chamber to a position outside the at least one capsule chamber or adjacent to the at least one capsule chamber;
a capsule opener disposed in front of the moveable back wall, the capsule opener attached to the housing or attached to the at least one capsule chamber; and
an incline feature connected to the housing disposed inline with the capsule opener behind the moveable back wall, the incline feature configured to bias the moveable back wall towards the capsule opener when the housing is rotated relative to the at least one capsule chambers about the common axis of rotation.

19. The device of claim 18, including an opening formed in a portion of the moveable back wall at a common radius to the incline feature, the opening configured accept the incline feature without moving the moveable back wall, and including an opening wall adjacent to the opening configured to prevent the capsule from passing through the opening.

20. The device of claim 19, wherein the moveable back wall is cantilevered and attached near an inner radius adjacent to the common axis of rotation and wherein the front wall of the housing comprises a thinning disposed adjacent to the capsule opener and aligned with the incline feature.

* * * * *